United States Patent
Berman et al.

(10) Patent No.: US 6,522,903 B1
(45) Date of Patent: Feb. 18, 2003

(54) GLUCOSE MEASUREMENT UTILIZING NON-INVASIVE ASSESSMENT METHODS

(75) Inventors: Herbert L. Berman, Los Altos Hills, CA (US); Jeffrey N. Roe, San Ramon, CA (US); Robert N. Blair, San Jose, CA (US)

(73) Assignee: MedOptix, Inc., Cupertino, CA (US)

( * ) Notice: Subject to any disclaimer, the term of this patent is extended or adjusted under 35 U.S.C. 154(b) by 0 days.

(21) Appl. No.: 09/693,202

(22) Filed: Oct. 19, 2000

(51) Int. Cl.$^7$ .................................................. A61B 5/00
(52) U.S. Cl. ........................ 600/316; 600/322; 600/365
(58) Field of Search ................................. 600/322–329, 600/309–311, 316, 365, 362; 356/39–42

(56) References Cited

U.S. PATENT DOCUMENTS

| | | |
|---|---|---|
| 4,169,676 A | 10/1979 | Kaiser |
| 4,427,889 A | 1/1984 | Müller |
| 4,538,618 A | 9/1985 | Rosenberg et al. |
| 4,655,255 A | 4/1987 | Rode |
| 4,710,231 A | 12/1987 | Bateman et al. |
| 4,821,733 A * | 4/1989 | Peck ........................... 600/361 |
| 4,909,256 A * | 3/1990 | Peck ........................... 600/362 |
| 5,028,787 A | 7/1991 | Rosenthal et al. |
| 5,036,861 A * | 8/1991 | Sembrowich et al. ....... 600/361 |
| 5,086,229 A | 2/1992 | Rosenthal et al. |
| 5,115,133 A | 5/1992 | Knudson |
| 5,178,142 A | 1/1993 | Harjunmaa et al. |
| 5,179,951 A | 1/1993 | Knudson |

(List continued on next page.)

FOREIGN PATENT DOCUMENTS

| | | |
|---|---|---|
| EP | 0 329 361 A2 | 8/1989 |
| WO | WO 96/19180 A1 | 6/1996 |
| WO | WO 97/29368 A1 | 8/1997 |

OTHER PUBLICATIONS

U.S. patent application Ser. No. 09/547,433, Berman et al., filed Apr. 12, 2000.

Bhandare, P. et al. (1993). "Multivariate Determination of Glucose in Whole Blood Using Partial Least–Squares and Artificiatl Neural Networks Based on Mid–Infrared Spectroscopy," *Appl. Spectr.* 47(8):1214–1221.

Ginsberg, B.H. (1992). "An overview of minimally invasive technologies," *Clin Chem.* 38(9):1596–1600.

Heise, H.M. et al. (1989). "Multivariate Determination of Glucose in Whole Blood by Attenuated Total Reflection Infrared Spectroscopy," *Anal Chem.* 61:2009–2015.

Hiese, H.M. et al. (1998). "Clinical Chemistry and Near Infrared Spectroscopy: Technology for Non–Invasive Glucose Monitoring," *J. Near Infrared Spectrosc.* 6:349–359.

Kajiwara, K. et al. (1992). "Spectroscopic Quantitative Analysis of Blood Glucose by Fourier Transform Infrared Spectroscopy with an Attenuated Total Reflection Prism," *Med. Prog. through Tech.* 18:181–189.

Klonoff, D.C. (Mar. 1997). "Noninvasive Blood Glucose Monitoring," *Diabetes Care* 20(3):433–437.

(List continued on next page.)

*Primary Examiner*—Max F. Hindenburg
*Assistant Examiner*—Matthew Kremer
(74) *Attorney, Agent, or Firm*—Morrison & Foerster LLP

(57) ABSTRACT

This involves non-invasive glucose measurement processes for determining blood glucose level in the human body. After achieving a static level of glucose at a surface of the skin over some period of time, the glucose may then be measured by a variety of different processes. A sample of the glucose may also first be extracted from the skin and this sample may then be measured. Clearly, these processes are especially suitable for monitoring glucose levels in the human body, and is especially beneficial to users having diabetes mellitus. These procedures may be used for other analyte materials that are found in appropriate regions of the outer skin.

17 Claims, 4 Drawing Sheets

U.S. PATENT DOCUMENTS

| | | | |
|---|---|---|---|
| 5,267,152 A | | 11/1993 | Yang et al. |
| 5,313,941 A | | 5/1994 | Braig et al. |
| 5,341,805 A | * | 8/1994 | Stavridi et al. ............. 600/316 |
| 5,390,238 A | | 2/1995 | Kirk et al. |
| 5,398,681 A | | 3/1995 | Kupershmidt |
| 5,433,197 A | | 7/1995 | Stark |
| 5,470,323 A | | 11/1995 | Smith et al. |
| 5,582,184 A | | 12/1996 | Erickson et al. |
| 5,638,815 A | * | 6/1997 | Shoendorfer ................ 600/346 |
| 5,682,233 A | | 10/1997 | Brinda |
| 5,749,217 A | | 5/1998 | Etheridge |
| 5,754,289 A | * | 5/1998 | Ozaki et al. ................. 356/301 |
| 5,820,570 A | | 10/1998 | Erickson et al. |
| 5,879,310 A | | 3/1999 | Sopp et al. |
| 5,879,367 A | | 3/1999 | Latterell et al. |
| 5,890,489 A | * | 4/1999 | Elden ......................... 128/898 |
| 5,941,821 A | * | 8/1999 | Chou .......................... 600/316 |
| 6,001,067 A | | 12/1999 | Shults et al. |
| 6,087,182 A | * | 7/2000 | Jeng et al. .................... 436/66 |
| 6,149,588 A | | 11/2000 | Noda et al. |
| 6,152,875 A | | 11/2000 | Hakamata |
| 6,188,477 B1 | * | 2/2001 | Pu et al. ...................... 356/351 |

OTHER PUBLICATIONS

Kruse–Jarres, J.D. et al. (Feb. 1990). "Glucose and Other Constituents of Blood Determined by ATR–FTIR–Spectroscopy," *Clin. Chem.* 36(2):401–402.

Mak, V.H. et al. (Aug. 1990). "Pecutaneous Penetration Enhancement in Vivo Measured by Attenuated Total Refelectance Infrared Spectroscopy." *Pharm. Res.* 7(8):835–841.

McNichols, R.J. and Coté, G.L. (Jan. 2000). "Optical glucose sensing in biological fluids: an overview," *J. Biomed. Optics* 5(1):5–16.

Mendelson, Y. et al. (1990). "Blood Glucose Measurement by Multiple Attenuated Total Reflection and Infrared Absorption Spectroscopy," *IEEE Trans. Biomed. Engin.* 37(5):458–465.

Potts, R.O. et al. (1985). "A Noninvasive, In Vivo Technique to Quantitatively Measure Water Concentration of the Stratum Corneum Using Attenuated Total–Reflectance Infrared Spectroscopy," *Arch. Dermatol. Res.* 277(6):489–495.

Rao, G. (Dec. 1993). "Reverse Iontophoresis: Development of a Noninvasive Approach for Glucose Monitoring," *Pharm Res.* 10(12):1751–1755.

Tucker, M.E. (Jan. 15, 2000). "FDA advisory panel backs wrist glucose monitor," *Intern. Med. News* 33(2):9.

\* cited by examiner

GLUCOSE MEASUREMENT UTILIZING NON-INVASIVE ASSESSMENT METHODS

FIELD OF THE INVENTION

This invention involves non-invasive glucose measurement and a process for determining blood glucose levels in the human body. Preferably, the process is used on a fingertip or other part of the body, typically a skin surface of the body.

BACKGROUND OF THE INVENTION

The American Diabetes Association reports that nearly 6% of the population in the United States, a group of 16 million people, has diabetes. The Association further reports that diabetes is the seventh leading cause of death in the United States, contributing to nearly 200,000 deaths per year. Diabetes is a chronic disease having no cure. The complications of the disease include blindness, kidney disease, nerve disease, and heart disease, perhaps with stroke. Diabetes is said to be the leading cause of new cases of blindness in individuals in the range of ages between 20 and 74; from 12,000–24,000 people per year lose their sight because of diabetes. Diabetes is the leading cause of end-stage renal disease, accounting for nearly 40% of new cases. Nearly 60–70% of people with diabetes have mild to severe forms of diabetic nerve damage which, in severe forms, can lead to lower limb amputations. People with diabetes are 2–4 times more likely to have heart disease and to suffer strokes.

Diabetes is a disease in which the body does not produce or properly use insulin, a hormone needed to convert sugar, starches, and the like into energy. Although the cause of diabetes is not completely understood, genetics, environmental factors, and viral causes have been partially identified.

There are two major types of diabetes: Type I and Type II. Type I diabetes (formerly known as juvenile diabetes) is an autoimmune disease in which the body does not produce any insulin and most often occurs in young adults and children. People with Type I diabetes must take daily insulin injections to stay alive.

Type II diabetes is a metabolic disorder resulting from the body's inability to make enough, or properly to use, insulin. Type II diabetes accounts for 90–95% of diabetes. In the United States, Type II diabetes is nearing epidemic proportions, principally due to an increased number of older Americans and a greater prevalence of obesity and a sedentary lifestyle.

Insulin, in simple terms, is the hormone that unlocks the cells of the body, allowing glucose to enter those cells and feed them. Since, in diabetics, glucose cannot enter the cells, the glucose builds up in the blood and the body's cells literally starve to death.

Diabetics having Type I diabetes typically are required to self-administer insulin using, e.g., a syringe or a pin with needle and cartridge. Continuous subcutaneous insulin infusion via implanted pumps is also available. Insulin itself is typically obtained from pork pancreas or is made chemically identical to human insulin by recombinant DNA technology or by chemical modification of pork insulin. Although there are a variety of different insulins for rapid-, short-, intermediate-, and long-acting forms that may be used variously, separately or mixed in the same syringe, use of insulin for treatment of diabetes is not to be ignored.

It is highly recommended by the medical profession that insulin-using patients practice self-monitoring of blood glucose (SMBG). Based upon the level of glucose in the blood, individuals may make insulin dosage adjustments before injection. Adjustments are necessary since blood glucose levels vary day to day for a variety of reasons, e.g., exercise, stress, rates of food absorption, types of food, hormonal changes (pregnancy, puberty, etc.) and the like. Despite the importance of SMBG, several studies have found that the proportion of individuals who self-monitor at least once a day significantly declines with age. This decrease is likely due simply to the fact that the typical, most widely used, method of SMBG involves obtaining blood from a finger stick. Many patients consider obtaining blood to be significantly more painful than the self-administration of insulin.

There is a desire for a less invasive method of glucose measurement. Methods exist or are being developed for a minimally invasive glucose monitoring, which use body fluids other than blood (e.g., sweat or saliva), subcutaneous tissue, or blood measured less invasively. Sweat and saliva are relatively easy to obtain, but their glucose concentration appears to lag in time significantly behind that of blood glucose. Measures to increase sweating have been developed and seem to increase the timeliness of the sweat glucose measurement, however.

Subcutaneous glucose measurements seem to lag only a few minutes behind directly measured blood glucose and may actually be a better measurement of the critical values of glucose concentrations in the brain, muscle, and in other tissue. Glucose may be measured by non-invasive or minimally-invasive techniques, such as those making the skin or mucous membranes permeable to glucose or those placing a reporter molecule in the subcutaneous tissue. Needle-type sensors have been improved in accuracy, size, and stability and may be placed in the subcutaneous tissue or peripheral veins to monitor blood glucose with small instruments. See, *"An Overview of Minimally Invasive Technologies"*, Clin. Chem. September 1992; 38(9) :1596–1600.

Truly simple, non-invasive methods of measuring glucose are not commercially available.

SUMMARY OF THE INVENTION

This invention involves non-invasive glucose measurement and a process for determining blood glucose levels in the human body upon achieving a static level of glucose at a skin surface over a period of time.

Processes which are able to assess glucose concentrations predictably from a skin surface may include a step of extracting a sample from the skin and then measuring that sample from the skin. Such sample extraction processes may include suction blister extraction, wick extraction, microdialysis extraction, iontophoretic extraction, sontophoretic extraction, and chemically enhanced extraction. Aside from the extraction processes, non-invasive measurement processes may include electrochemical sensors (e.g., glucose electrodes), optochemical sensors (e.g., colorimetric strips), near-infrared spectroscopy (NIR), mid-infrared spectroscopy (MIR), infrared spectroscopy (IR), Raman spectroscopy, photoacoustic spectroscopy, measurement of refractive index or scatter changes, fluorescent spectroscopy, and polarization spectroscopy.

The processes for extraction and measurement are illustrative and are not meant to be an exclusive list.

DESCRIPTION OF THE INVENTION

Figure 1:
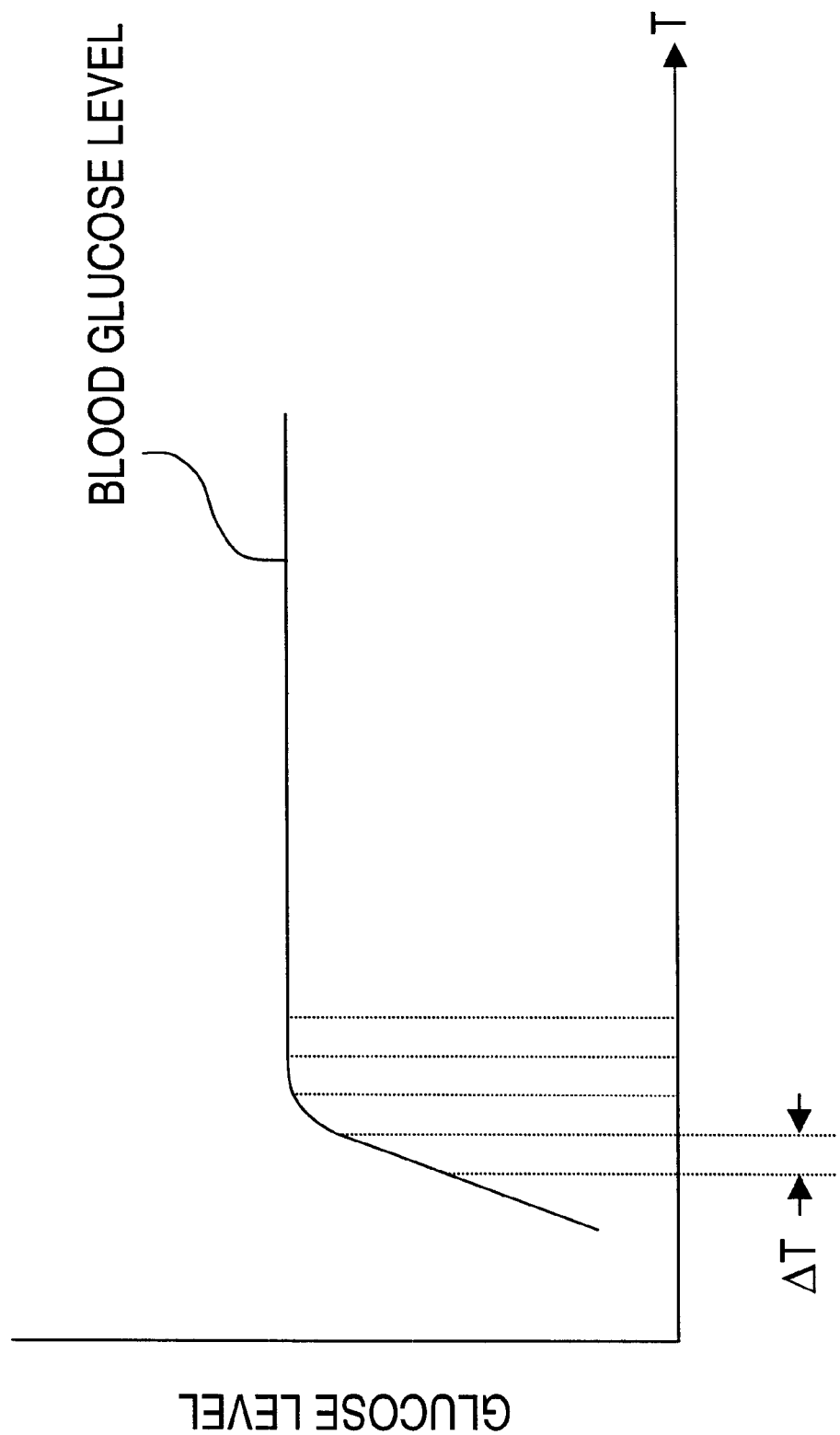
FIG. 1 shows a graph representing a glucose level rising sharply and reaching a static value.

In non-invasively measuring analyte levels using mid-infrared ("MIR"), particularly using a device and methods as described in U.S. patent application Ser. No. 09/547,433, filed Apr. 12, 2000, entitled "INFRARED ATR GLUCOSE MEASUREMENT SYSTEM (II)", which is herein incorporated by reference in its entirety, penetration of skin by IR ranged in only a few micrometers. Thus, because of this small penetration depth, the described device may have been measuring glucose from the mixture of oils and sweat that is pumped to the skin surface. Therefore, multiple alternative processes may be utilized in non-invasively measuring analytes, particularly glucose, from a skin surface.

The device in co-pending application Ser. No. 09/547,433 described the use of IR attenuated total reflectance ("ATR") spectroscopy to detect and ultimately to determine the level of a selected analyte, preferably blood glucose, in the human body. Preferably, the inventive device used an ATR procedure in which the size and configuration of the crystal permits a number of internal reflections before the beam is allowed to exit the crystal with its measured information.

We have found that the mid-IR spectrum does not penetrate into the skin to an appreciable level. Specifically, the skin is made up of a number of layers: the outermost—the stratum corneum—is a layer substantially free of interference from cholesterol, water, gamma globulin, albumin, and blood. It is a shallow outer region covering the stratum granulosum, the stratum spinosum, and the basal layer. The area between the basal layer to the outside is not vascularized. It is unlikely that any layer other than the stratum corneum is traversed by the mid-IR light involved in this inventive device. Although we do not wish to be bound by theory, it is likely that the eccrine or sweat glands transport the glucose to the outer skin layers for measurement and analysis by our inventions.

We have surprisingly found that a glucose measuring device made according to the invention in application Ser. No. 09/547,433 is quite effective on the human skin of the hands and fingers. We have found that the glucose concentration as measured by the inventive devices correlates very closely with the glucose concentration determined by a direct determination from a blood sample. This is surprising in that the IR beam likely passes into the skin, i.e., the stratum corneum, for only a few microns. It is unlikely in a fingertip that any blood is crossed by that light path. As discussed above, the stratum corneum is the outer layer of skin and is substantially unvascularized. The stratum corneum is the final outer product of epidermal differentiation or keratinization. It is made up of a number of closely packed layers of flattened polyhedral corneocytes (also known as squames). These cells overlap and interlock with neighboring cells by ridges and grooves. In the thin skin of the human body, this layer may be only a few cells deep, but in thicker skin, such as may be found on the toes and feet, it may be more than 50 cells deep. The plasma membrane of the corneocyte appears thickened compared with that of keratinocytes in the lower layers of the skin, but this apparent deposition of a dense marginal band formed by stabilization of a soluble precursor, involucrin, just below the stratum corneum.

It is sometimes necessary to clean the skin exterior prior before sampling to remove extraneous glucose from the skin surface. At least when using IR spectra to measure glucose, it is important to select cleaning materials having IR spectra that do not interfere with the IR spectra of glucose. We consider a kit of the following to be suitable for preparation of the sample skin for the testing. The components are: a.) a glucose solvent, e.g., water or other highly polar solvent; b.) a solvent for removing the water, e.g., isopropanol, and c.) a skin softener or pliability enhancer not having significant IR peaks in the noted IR regions, e.g., mineral oils such as those sold as "Nujol". Preferably the b.) and c.) components are admixed, although they need not be. Certain mixtures of the first two components may be acceptable, but only if the sampling situation is such that the solvents evaporate without IR spectrographically significant residue. We have also found that soap and its residue are sometimes a problem. Consequently, addition of a weak acid again not having significant IR peaks in the noted IR regions, to the a.) component, i.e., the solvent for removing glucose, is desirable. The preferred weak acid is boric acid. The inventive kit preferably is made up of sealed packets of the components, most preferably each packet containing an absorbent pad.

Method of Use

As noted in application Ser. No. 09/547,433, for IR measurement, it is desirable both to clean the plate before use and to clean the exterior surface of the skin to be sampled. Again, we have found that the exterior skin is highly loaded with glucose that is easily removed preferably by using the skin preparation kit, or, less preferably, by washing the skin. Reproducible and accurate glucose measurements may then be had in a period as short as one to ten minutes, generally less than five minutes, after cleaning the area of the skin to be measured.

We also note that, depending upon the design of a specific variation of a device made according to the invention, periodic at least an initial calibration of the device, using typical blood sample glucose determinations, may be necessary or desirable.

Alternate Methods of Use

We have also observed the following phenomena. In attempting to measure glucose using the mid IR apparatus described above, we noted that by using a solvent on the surface which dissolved glucose, our procedures showed that the glucose level at the skin was substantially lowered, if not eliminated. However, as is shown in the examples, shortly thereafter, the glucose level began to rise sharply and consequently would reach static value which was correlateable in a consistent fashion to a glucose level found in the blood.

As shown in FIG. 1, the curve representing the glucose level rises sharply and eventually plateaus over a time period, T. This glucose level may be measured by any of the devices and processes as discussed in application Ser. No. 09/547,433 or herein at predetermined time periods, $\Delta T$, until the glucose level reaches a substantially static value, thus representing the glucose level in the blood. As we have noted above, the outer layer of the skin is not vascularized and the physiological source of the glucose transport to the skin surface is not all together clear. Nevertheless, it is easily assessable and quite repeatable. Our method of using mid IR to measure this glucose level is believed, on basic principals, only to penetrate the skin at best a few microns. Other procedures which are non-invasive and which are able to assess glucose concentration upon this achievement of glucose stasis level are similarly and predictably able to assess the glucose level in the human body.

Such alternative procedures may provide for extracting a sample from the skin and then measuring the analyte, or glucose, level in the sample. Potential extraction methods may include blister suction and wick extraction, microdialysis extraction, iontophoretic extraction, sontophoretic extraction, and chemically enhanced extraction.

Sample measurement methods may include electrochemical sensors (e.g., glucose electrodes), optochemical sensors (e.g., colorimetric strips), near-infrared spectroscopy (NIR), infrared spectroscopy (IR), Raman spectroscopy, photoacoustic spectroscopy, measurement of refractive index or scatter changes, fluorescent spectroscopy, and polarization spectroscopy. These methods of sample extraction and measurement are provided.

Glucose Extraction

Blister suction and wick extraction are some of the most common methods for sampling subcutaneous interstitial tissue fluid, although blister extraction is less invasive than the wick extraction technique. Microdialysis extraction involves calculating the concentrations of compounds, including skin glucose concentrations, which are in the extracellular water space. Microdialysis has been applied to peripheral tissue types, e.g., skin, muscle, adipose, eye, lung, liver, and blood as well as having microdialysis probes implanted subcutaneously and perfused by a portable microinfusion pump. Finally, iontophoretic extraction involves noninvasive glucose measurement from subcutaneous tissue.

Glucose Measurement

Electrochemical Sensors

Electrochemical sensors (e.g., glucose electrodes) utilize electrical signal as a direct consequence of some (chemical) process occurring at a transducer/analyte interface. Some implantable glucose sensors may include electrocatalytic sensors, which are based on direct electro-oxidation of glucose on noble metal electrodes, and biosensors, which combine glucose-specific enzymes with electrochemical electrodes.

Such sensors may be fabricated by combining biologically active components (e.g., enzymes, antibodies, cells, tissues or microorganisms) with some physical transducer. Biosensors may be direct enzyme biosensors or affinity sensors based on enzyme labeled immunoassays. Enzymes may be used as a molecular recognition element in glucose sensing while immunoassays may provide the ability to sense extremely low amounts of an ahalyte. Electrochemical sensors may also include piezoelectric, thermoelectric, and acoustic sensors used for glucose measurement by utilizing an enzyme-catalysed reaction to create a measurable change in a physical parameter detectable by a transducer.

Optochemical Sensors

Optochemical sensors (e.g., colorimetric strips) are based on changes in some optical parameter due to enzyme reactions or antibody-antigen bonding at a transducer interface. Such sensors may include enzyme optrodes and optical immunosensors and may also include different monitoring processes such as densitometric, refractometric or calorimetric devices.

Electrochemical biosensors may be constructed on the amperometric principle which is based on the oxidation or reduction of electrochemically active substances. Such sensor may also be constructed to measure the changes in local pH due to the gluconic acid produced at a potentiometric sensor, usually a coated wire pH-selective electrode or an ion selective field effect transistor (ISFET). Also, electrical resistance changes during the overall process may be used as a basis for conductometric biosensors.

Moreover, potentiometric glucose sensors (e.g., coated wire sensors) may potentially be utilized for implantable use. Coated wire sensors are general easy to fabricate and are suitable for miniaturization to diameters of 50–200 $\mu$m. They may also be used in combination with a standard cardiographic (EKG) reference electrode.

Near-Infrared Spectroscopy (NIR)

The NIR region of the spectrum extends from 700 to 2500 nm (14,000–4000 cm$^-$). In this region, absorption bands are due to overtone vibrations of anharmonic fundamental absorption bands to combinations of fundamental absorption bands primarily associated with C—H; O—H, and N—H stretching vibrations. For overtone vibrations, only the first, second, and third overtones are usually seen with the magnitude of the absorption peak diminishing substantially with overtone order. The NIR region may be attractive for quantitative spectroscopy since NIR instrumentation is readily available.

In measuring aqueous glucose, the NIR region which lies between 2.0 and 2.5 $\mu$m may be utilized. This region contains a relative minimum in the water absorption spectrum and has readily identifiable glucose peak information. However, NIR spectra may generally be sensitive to a host of factors including temperature, pH, and scattering.

Raman Spectroscopy

Raman spectra are typically observed when incident light at a frequency $v_0 = c/\lambda_0$ is inelastically scattered at frequencies $v_0 \pm v_i$. The loss (Stokes shift) or gain (anti-Stokes shift) of photon energy, and hence frequency, is due to transitions of the rotational and vibrational energy states within the scattering molecule. Since the Raman spectrum is independent of excitation frequency, an excitation frequency may be chosen which is appropriate for a particular sample. However, a drawback may be that scatter and reabsorption in biological tissues may make detection of Raman shifts due to physiological concentrations difficult.

Photoacoustic Laser Spectroscopy

Photoacoustic laser spectroscopy has been utilized for measuring glucose concentrations of human whole blood samples using pulsed laser photoacoustic spectroscopy. Such a process may use, e.g., a $CO_2$ laser operating with $\mu$J pulse energy, to measure tiny changes of the absorption coefficient of the sample caused by the variations of blood glucose concentrations.

Refractive Index or Scatter Changes

Measurement of refractive index or scatter changes may be feasible to measure blood glucose by measuring the scattering coefficient of human skin, e.g., by using optical sensors attached to the skin. Such techniques may be based on the fact that the refractive index of sugar solution changes with the concentration of sugar.

Fluorescent Spectroscopy

There may be two categories for fluorescent spectroscopy: glucose-oxidase based sensors and affinity-binding sensors. Sensors in the first category may use the electroenzymatic oxidation of glucose by glucose-oxidase (GOX) in order to generate an optically detectable glucose-dependent signal. The oxidation of glucose and oxygen forms gluconolactone and hydrogen peroxide.

Several methods for optically detecting the products of this reaction, and hence the concentration of glucose driving the reaction, may be utilized. Since oxygen is consumed in this reaction at a rate dependent on the local concentration of glucose, a fluorophore which is sensitive to local oxygen concentration can also be used to quantify glucose concentration.

A method GOX based fluorescent sensor involves the redox mediator tetrathiafulvalene (TTF) whose oxidized form TTF$^+$ reacts with the reduced form of GOX to reversibly form TTF$^0$. Since TTF$^+$ is absorbed in the 540–580 nm range, a method for quantifying the presence of TTF$^+$ (and hence glucose driving the production of reduced GOX) is available.

Another method involves the hydrogen peroxide ($H_2O_2$) generated from the GOX reaction with glucose reacting with bis(2,4,6-trichlorophenyl) oxalate (TCPO) to form a peroxyoxylate. Here, the peroxyoxylate formed transfers chemiluminescent energy to an accepting fluorophore which in turn emits photons at a characteristic wavelength. The emission by the fluorophore is proportional to the glucose concentration and may be detected optically.

Polarization Spectroscopy

Polarimetric quantification of glucose may be based on the principle of optical rotary dispersion (ORD) where a chiral molecule in an aqueous solution rotates the plane of linearly polarized light passing through the solution. This rotation is due to a difference in the indices of refraction $n_L$ and $n_R$ for left- and right-circularly polarized light passing through a solution containing the molecule. Because the molecule has a chirality (or "handedness"), the angle of rotation depends linearly on the concentration of the chiral species, the path length through the sample, and a constant for the molecule called the specific rotation. Glucose in the body is dextrorotatory, i.e., rotates light in a right-handed direction, and has a specific rotation of +52.6° dm$^{-1}$ (g/L)$^{-1}$.

EXAMPLES OF MID-IR USE

Example 1

Using a commercially available IR spectrometer (Nicolet 510) having a ZnSe crystal ATR plate (55 mm long, 10 mm wide, and 4 mm thick) we tested the inventive procedure. We calibrated the output of the spectrometer by comparing the IR signal to the values actually measured using one of the inventor's blood samples. The inventor used a blood stick known as "Whisper Soft" by Amira Medical Co. and "Glucometer Elite" blood glucose test strips sold by Bayer Corp. of Elkhart, Ind. On each of the various test days, the inventor took several test sticks and measured the glucose value of the resulting blood; the IR test was made at the same approximate time.

Figure 2:
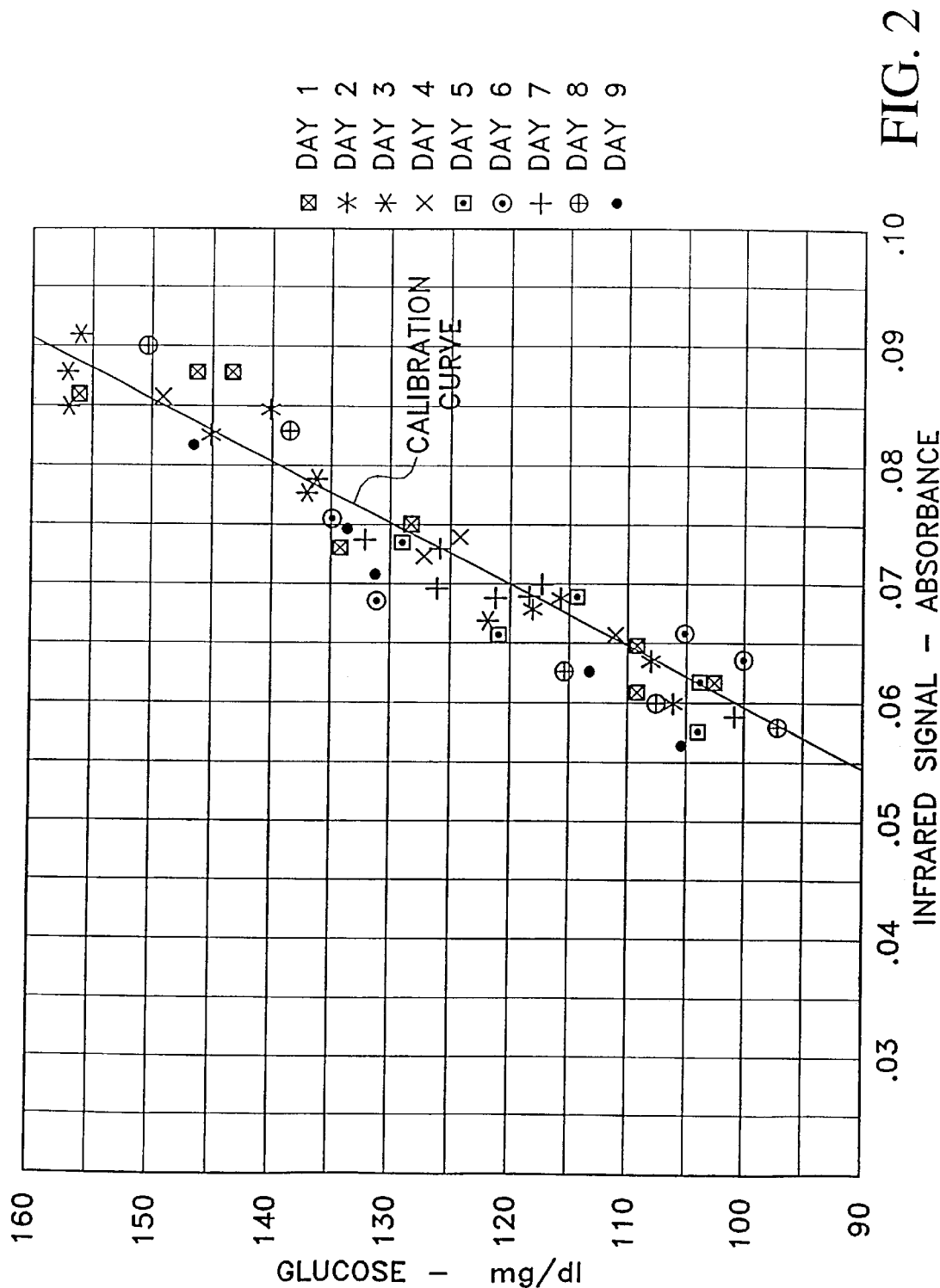
FIG. 2 shows a graph correlating glucose levels measured using a specific variation of the device with glucose levels in the blood determined using a commercial device.

As shown in the calibration curve of FIG. 2, the data are quite consistent. So, where the blood glucose concentration "B" is in (mg/dl) and "S" is the difference between the absorbance at the referencing region and the measuring region as measured by the spectrometer:

$B = [(1950) \cdot S] - (17)$.

Example 2

Figure 3:
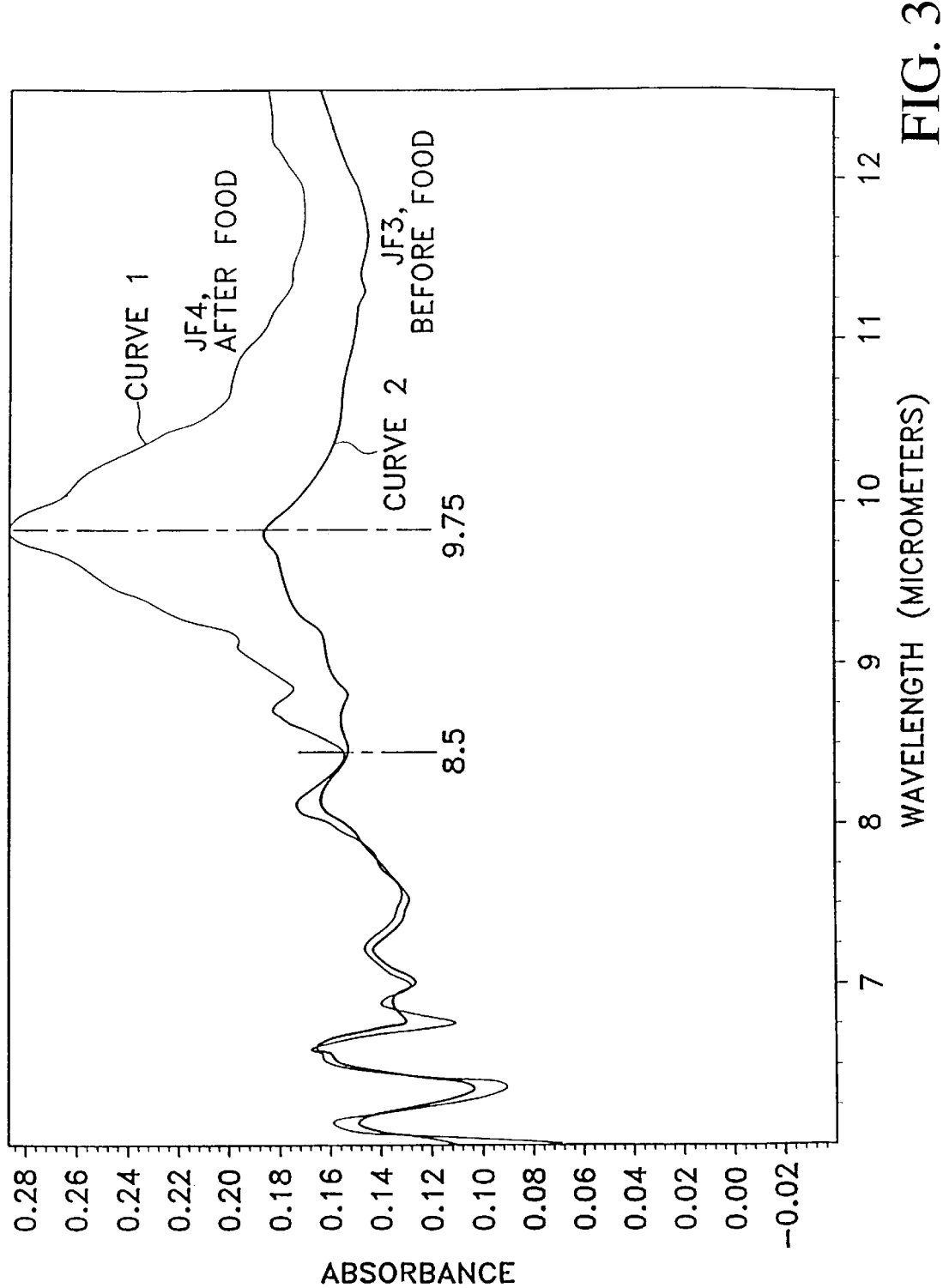
FIG. 3 shows a pair of glucose IR curves (taken before and after eating) for an individual having diabetes made using the inventive glucose measuring device.

In accordance with a clinical protocol, a diabetic was then tested. Curve 1 in FIG. 3 shows the IR absorbance spectrum of the test subject's finger before eating (and after fasting overnight) and curve 2 shows IR absorbance spectrum of the same individual after having eaten. Incidentally, insulin was administered shortly after the measurement of curve 2.

In any event, the significant difference in the two peak heights at the 9.75 micrometer wavelength and the equality of the two IR absorbance values at the 8.50 micrometer value shows the effectiveness of the procedure in measuring glucose level.

Example 3

Figure 4:
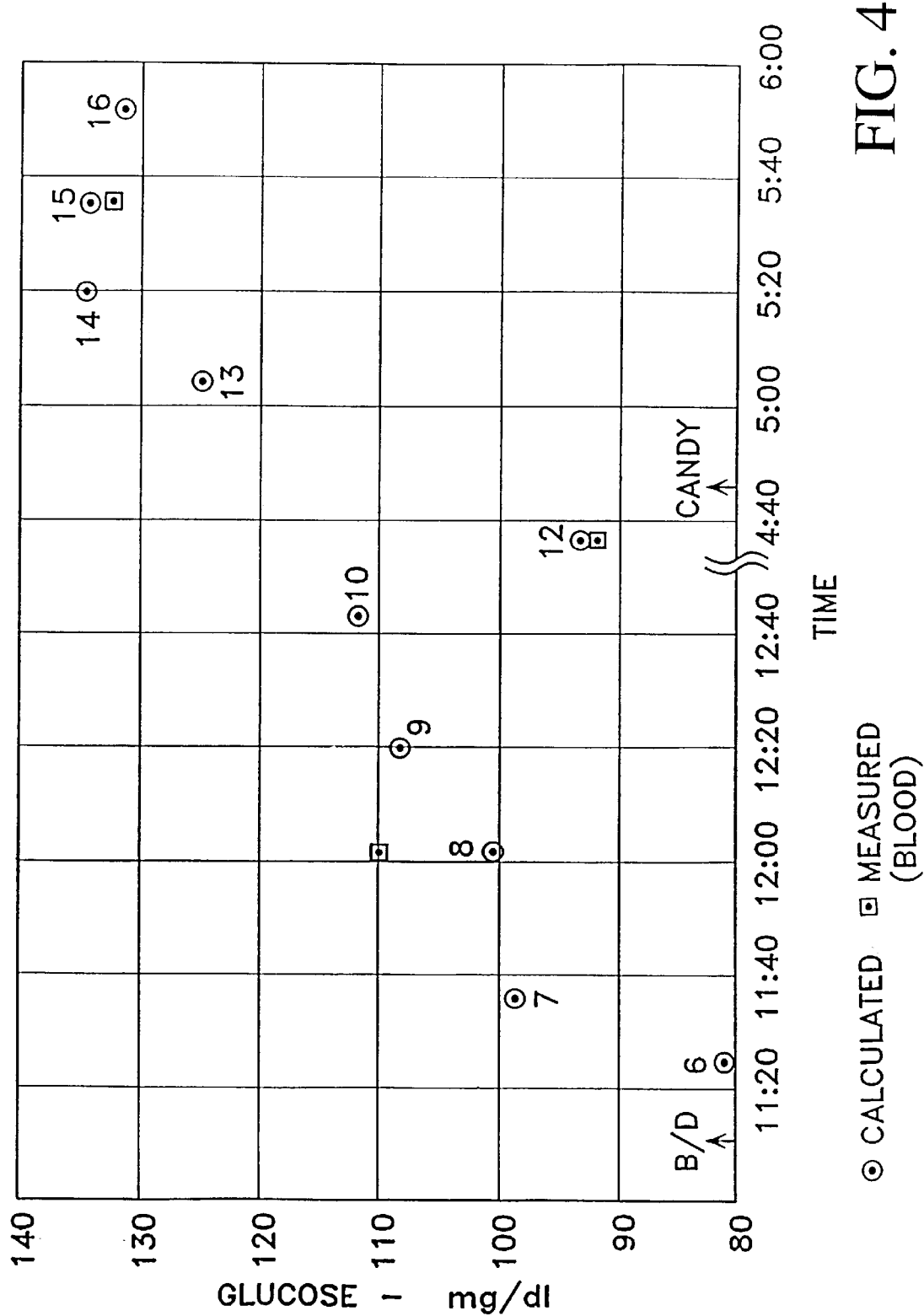
FIG. 4 shows a graph comparing glucose levels in a non-diabetic individual (taken before and after eating) made using the inventive glucose measuring device and direct blood measurement. This graph shows that the inventive procedure tracks blood glucose levels with minimum time lag.

That the inventive glucose monitoring device non-invasively determines blood glucose level and quickly follows changes in that blood glucose level is shown in FIG. 4. Using both the inventive procedure and a commercial glucose device, one of the inventors followed his glucose level for a single day. The blood sticks are considered to be accurate within 15% of the actual reading.

The results are shown in FIG. 4. Of particular interest is the measurement just before 4:40 pm wherein the two values are essentially the same. A high sugar candy bar was eaten at about 4:45pm and measurements of glucose level were taken using the inventive procedure at about 5:03, 5:18, 5:35 and 5:50. A blood sample was taken at 5:35 and reflected almost the same value as that measured using the inventive procedure. Consequently, the procedure tracks that measured by the blood very quickly.

This invention has been described and specific examples of the invention have been portrayed. The use of those specifics is not intended to limit the invention in any way. Additionally, to the extent there are variations of the invention with are within the spirit of the disclosure and yet are equivalent to the inventions found in the claims, it is our intent that this patent will cover those variations as well.

We claim as our invention:

1. A process for determining a glucose level of a human body, comprising the steps of:
    a.) cleaning a skin surface on said human body;
    b.) achieving a non-induced static level of glucose at the skin surface as measured over a period of time, wherein the static level is correlateable to the glucose level of the human body; and
    c.) measuring said skin surface glucose level.

2. The process of claim 1, wherein the step of measuring further comprises:
    a.) extracting a sample from the skin surface, and
    b.) measuring the glucose level from the sample.

3. The process of claim 2, wherein the step of extracting is selected from the group consisting of blister suction, wick extraction, microdialysis extraction, iontophoretic extraction, sontophoretic extraction, and chemically enhanced extraction.

4. The process of claim 1, wherein the step of measuring comprises electrochemical sensors.

5. The process of claim 4, wherein the electrochemical sensors comprise glucose electrodes.

6. The process of claim 1, wherein the step of measuring comprises optochemical sensors.

7. The process of claim 6, wherein the optochemical sensors comprise colorimetric strips.

8. The process of claim 1, wherein the step of measuring comprises near-infrared spectroscopy.

9. The process of claim 1, wherein the step of measuring comprises Raman spectroscopy.

10. The process of claim 1, wherein the step of measuring comprises photoacoustic spectroscopy.

11. The process of claim 1, wherein the step of measuring comprises measuring a refractive index or scatter changes of the sample.

12. The process of claim 1, wherein the step of measuring comprises fluorescent spectroscopy.

13. The process of claim 1, wherein the step of measuring comprises polarization spectroscopy.

14. The process of claim 1 wherein the period of time is less than six hours.

15. The process of claim 1 wherein the period of time is less than one hour.

16. The process of claim 1 wherein the period of time is less than ten minutes.

17. The process of claim 1 wherein the period of time is less than five minutes.

* * * * *

UNITED STATES PATENT AND TRADEMARK OFFICE
CERTIFICATE OF CORRECTION

PATENT NO. : 6,522,903 B1
DATED : February 18, 2003
INVENTOR(S) : Herbert L. Berman et al.

It is certified that error appears in the above-identified patent and that said Letters Patent is hereby corrected as shown below:

<u>Title page,</u>
Item [*], Notice, please replace "0 days" with -- 45 days --.

Signed and Sealed this

Tenth Day of June, 2003

JAMES E. ROGAN
*Director of the United States Patent and Trademark Office*